United States Patent
Ueda et al.

(10) Patent No.: US 9,541,483 B2
(45) Date of Patent: Jan. 10, 2017

(54) CONTACT STATE OBSERVATION APPARATUS OF GOLF BALL AND CONTACT STATE OBSERVATION METHOD OF GOLF BALL

(71) Applicants: BRIDGESTONE CORPORATION, Chuo-ku, Tokyo (JP); BRIDGESTONE SPORTS CO., LTD, Minato-ku, Tokyo (JP)

(72) Inventors: Hiroyuki Ueda, Fuchu (JP); Kazuo Uchida, Fuchu (JP); Atsushi Komatsu, Chichibu (JP); Wataru Ban, Chichibu (JP)

(73) Assignees: BRIDGESTONE CORPORATION, Tokyo (JP); BRIDGESTONE SPORTS CO., LTD, Tokyo (JP)

( * ) Notice: Subject to any disclaimer, the term of this patent is extended or adjusted under 35 U.S.C. 154(b) by 0 days.

(21) Appl. No.: 14/677,278

(22) Filed: Apr. 2, 2015

(65) Prior Publication Data

US 2015/0306468 A1   Oct. 29, 2015

(30) Foreign Application Priority Data

Apr. 23, 2014  (JP) ................. 2014-088977

(51) Int. Cl.
| | |
|---|---|
| G01N 3/30 | (2006.01) |
| G01N 3/52 | (2006.01) |
| G01N 3/56 | (2006.01) |
| G01N 19/02 | (2006.01) |
| G01N 3/06 | (2006.01) |

(52) U.S. Cl.
CPC ............... *G01N 3/068* (2013.01); *G01N 3/30* (2013.01)

(58) Field of Classification Search
None
See application file for complete search history.

(56) References Cited

U.S. PATENT DOCUMENTS

| | | | | |
|---|---|---|---|---|
| 2,715,338 A | * | 8/1955 | Simjian | A63B 69/0079 473/141 |
| 6,764,412 B2 | * | 7/2004 | Gobush | A63B 24/0003 382/164 |
| 6,781,621 B1 | * | 8/2004 | Gobush | A63B 69/3614 348/135 |

(Continued)

FOREIGN PATENT DOCUMENTS

JP   2006-343139 A   12/2006

*Primary Examiner* — Peter Macchiarolo
*Assistant Examiner* — Jermaine Jenkins
(74) *Attorney, Agent, or Firm* — Sughrue Mion, PLLC

(57) ABSTRACT

A contact state observation apparatus of golf ball can observe the contact phenomenon between a golf ball and a golf club which has been conventionally hidden and unobservable. The contact state observation apparatus of golf ball includes: launching means for launching a golf ball 10; an impact plate 20 with which the launched golf ball 10 impacts; and imaging means 30, provided opposite to the launching means across the impact plate 20, for shooting an image of the contact state between the golf ball 10 and the impact plate 20 at the time of impact of the golf ball 10. The impact plate 20 has, in a part where the golf ball 10 impacts, an observation hole 21 whose area is smaller than a contact area with the golf ball, and the imaging means 30 shoots the image of the contact state through the observation hole 21.

7 Claims, 7 Drawing Sheets

(56) References Cited

U.S. PATENT DOCUMENTS

| | | | | |
|---|---|---|---|---|
| 7,151,178 B2 * | 12/2006 | Caudill | ................ | C07D 241/24 |
| | | | | 544/406 |
| 7,441,438 B2 * | 10/2008 | Bissonnette | ....... | A63B 69/3658 |
| | | | | 73/1.01 |
| 7,454,948 B2 * | 11/2008 | Tsunoda | ................. | G01N 19/02 |
| | | | | 73/11.01 |
| 7,503,858 B2 * | 3/2009 | Cameron | ........... | A63B 24/0003 |
| | | | | 473/407 |
| 9,261,445 B2 * | 2/2016 | Peters | ................ | G09B 19/0038 |
| 2005/0261071 A1 * | 11/2005 | Cameron | ........... | A63B 24/0003 |
| | | | | 473/219 |

* cited by examiner

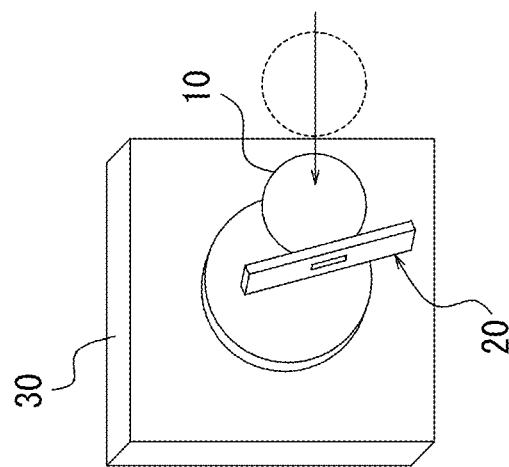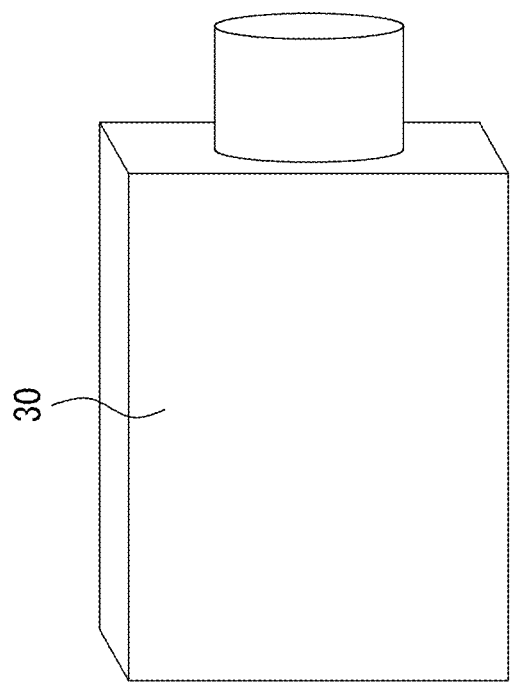
FIG. 5

TEST SURFACE 1    TEST SURFACE 2

US 9,541,483 B2

CONTACT STATE OBSERVATION APPARATUS OF GOLF BALL AND CONTACT STATE OBSERVATION METHOD OF GOLF BALL

TECHNICAL FIELD

The present invention relates to a contact state observation apparatus of golf ball and a contact state observation method of golf ball.

BACKGROUND

Golfers have a constant desire to hit long and accurate shots. In developing higher performance golf balls or golf clubs to meet this desire, it is very important to analyze the contact phenomenon between a golf ball and a golf club.

However, the following factors cause difficulty in analyzing what kind of phenomenon occurs on the contact surface between the golf ball and the golf club.

(1) The duration of the contact phenomenon between the golf ball and the golf club is short (about 0.5 msec).

(2) Since the contact phenomenon is significantly influenced by the contact surface with the golf club, it is desirable to recognize the state of the contact surface, but the contact surface is hidden and is unobservable.

The factor (1) can be solved by using a high-speed camera or the like.

The factor (2), however, remains unsolved, and there is the need to develop a technique that can solve the problem. Forces acting on the ball include the contact force from the club. The contact force can be divided into a normal direction component and a friction force component. In particular, the friction force changes significantly due to, for example, small slippage of the contact surface. Conventional study has revealed that the spin of the ball changes when the club surface (material, grooves, surface roughness, etc.) is changed, which may significantly affect the carry in the case of drivers and the force of stopping (accuracy) after landing in the case of irons.

As a technique for predicting the amount of spin of a golf ball, for example, Patent Literature (PTL) 1 discloses the following method of measuring the coefficient of kinetic friction of a golf ball and an impact plate tilted at a predetermined angle with respect to the flight direction of the golf ball when the golf ball impacts the impact plate: The time function of the contact force in the direction perpendicular to the impact plate and the time function of the contact force in the direction parallel to the impact plate are simultaneously determined, and the coefficient of kinetic friction is calculated based on a specific relational expression.

CITATION LIST

Patent Literature

PTL 1: JP 2006-343139 A

With the technique disclosed in PTL 1, the amount of spin of the golf ball can be predicted, but the contact phenomenon between the gold ball and the golf club cannot be observed. As mentioned above, recognizing the contact phenomenon between the golf ball and the golf club is very important for more accurate understanding of the behavior of the golf ball.

In view of the problem stated above, the present invention has an object of providing a contact state observation apparatus of golf ball and a contact state observation method of golf ball that can reproduce and observe the contact state between a golf ball and a golf club which has been conventionally hidden and unobservable.

SUMMARY

As a result of intensive research to solve the stated problem, the inventors discovered that the contact phenomenon with a golf ball, which has been conventionally hidden and unobservable, can be reliably observed by, through the use of launching means for launching a golf ball, an impact plate with which the launched golf ball impacts, and imaging means provided opposite to the launching means with the impact plate in between for shooting an image of the contact state between the golf ball and the impact plate at the time of impact of the golf ball, shooting the image of the contact state of the golf ball through a specific observation hole formed in a part of the impact plate where the golf ball impacts, thereby completing the present invention.

Primary features of the present invention are as follows.

A contact state observation apparatus of golf ball according to the present invention includes: launching means for launching a golf ball; an impact plate with which the launched golf ball impacts; and imaging means, provided opposite to the launching means with the impact plate in between, for shooting an image of a contact state between the golf ball and the impact plate at the time of impact of the golf ball, wherein the impact plate has, in a part where the golf ball impacts, an observation hole whose area in a surface facing the launching means is smaller than a contact area with the impacting golf ball, and the imaging means shoots the image of the contact state of the golf ball through the observation hole.

This enables the reproduction and observation of the contact phenomenon between the golf ball and the golf club.

Preferably, the area of the observation hole is 1% to 40% of the contact area between the impact plate and the golf ball. More preferably, the observation hole has a horizontal width of 1 mm to 10 mm. This enables more accurate reproduction of the contact phenomenon between the golf ball and the golf club.

Preferably, the observation hole is tapered in the impact plate from a surface facing the imaging means toward the surface facing the launching means. This eases the admission of a light source during observation.

Preferably, the observation hole is filled with a transparent material. This enables more accurate reproduction of the deformation state of the golf ball upon the contact.

Preferably, the surface of the impact plate facing the launching means is processed corresponding to a surface shape of a golf club. This enables the reproduction of the contact phenomenon between the actual golf club and golf ball.

Preferably, the contact state observation apparatus of golf ball further includes a load meter for measuring a force at the time of impact between the impact plate and the golf ball. This enables accurate recognition of the force acting on the golf ball upon the contact. In this respect, it is more preferable to use a two-component force meter, a three-component force meter, or the like as the load meter.

A contact state observation method of golf ball according to the present invention is a method of launching a golf ball, causing the launched golf ball to impact an impact plate, and observing a contact state of the golf ball with the impact plate at the time of impact, wherein an observation hole whose area is smaller than a contact area with the impacting golf ball is formed in a part of the impact plate where the golf ball impacts, and the contact state of the golf ball with the impact plate is observed through the observation hole.

This ensures the observation of the contact phenomenon between the golf ball and the golf club.

According to the present invention, it is possible to provide a contact state observation apparatus of golf ball and a contact state observation method of golf ball that can reproduce and observe the contact state between a golf ball and a golf club which has been conventionally hidden and unobservable.

BRIEF DESCRIPTION OF THE DRAWINGS

The present invention will be further described below with reference to the accompanying drawings, wherein:

FIG. 5 is a side view schematically illustrating another embodiment of the contact state observation apparatus of golf ball according to the present invention;

DETAILED DESCRIPTION

The present invention is described in detail below, based on embodiments.
(Contact State Observation Apparatus of Golf Ball)

An embodiment of a contact state observation apparatus of golf ball according to the present invention is described first.

Figure 1:
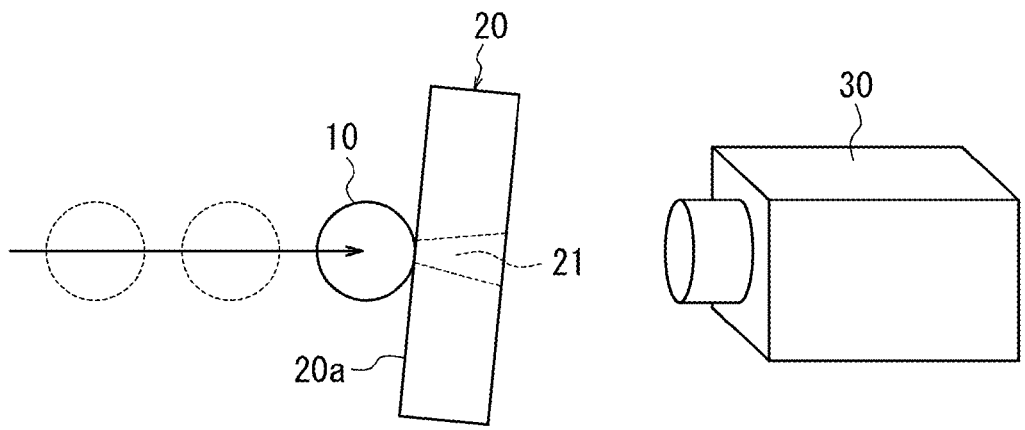
FIG. 1 is a side view schematically illustrating an embodiment of a contact state observation apparatus of golf ball according to the present invention.

As illustrated in FIG. 1, the contact state observation apparatus of golf ball according to the present invention includes: launching means (not illustrated) for launching a golf ball 10; an impact plate 20 with which the launched golf ball 10 impacts; and imaging means 30, provided opposite to the launching means with the impact plate 20 in between, for shooting an image of the contact state between the golf ball 10 and the impact plate 20 at the time of impact of the golf ball 10.

In the present invention, the impact plate 20 has, in a part where the golf ball 10 impacts, an observation hole 21 whose area in a surface (hereafter referred to as a "impact surface" according to need) 20a facing the launching means is smaller than the contact area with the impacting golf ball 10, and the imaging means 30 shoots the image of the contact state of the golf ball 10 through the observation hole 21.

By observing the contact state between the golf ball 10 and the impact plate 20 through the observation hole 21, the contact phenomenon with the golf ball, which has been conventionally hidden and unobservable, can be reliably observed. In addition, by changing the properties (material, grooves, surface roughness, etc.) of the impact surface of the impact plate with the golf ball according to the intended golf club as required, the contact state between the actual golf club and golf ball can be reproduced with high accuracy.

Note that the golf ball used in the contact state observation apparatus of golf ball according to the present invention is not particularly limited as long as it is a golf ball whose contact state is to be observed, and various golf balls may be used.

For example, a golf ball conforming to the standard that the diameter is not less than 1.680 inches and the weight is not greater than 45.93 g may be used. If the standard is changed in the future, a golf ball conforming to the changed standard may be used to observe its contact state. The material of the surface or inside of the golf ball is also not particularly limited in the present invention.

Launching Means

The contact state observation apparatus of golf ball according to the present invention includes the launching means (not illustrated) for launching the golf ball 10.

The launching means is not particularly limited as long as it is capable of launching the golf ball to a required position at a required velocity. For example, a commercially available golf ball launcher may be used. Launching means capable of launching the golf ball with no rotation is preferable for observation.

Impact Plate

The contact state observation apparatus of golf ball according to the present invention includes the impact plate 20 with which the launched golf ball 10 impacts, as illustrated in FIG. 1.

In actual golf, a golf club impacts with a golf ball. In the present invention, the golf ball 10 is caused to impact the impact plate 20 while taking into consideration the swing speed of the golf club and the loft angle and face angle of the face of the golf club head, with it being possible to simulatively reproduce the contact state between the golf club and the golf ball at the moment when the golf club strikes the golf ball.

Figure 2:
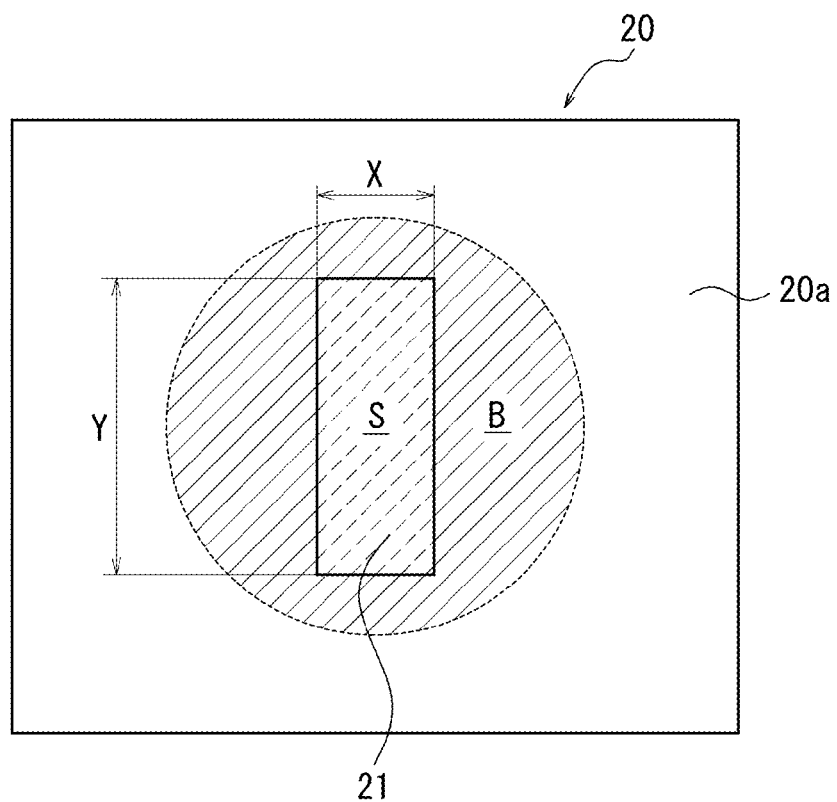
FIG. 2 is a front view schematically illustrating an impact plate in the embodiment of the contact state observation apparatus of golf ball according to the present invention.

As illustrated in FIG. 2, the impact plate 20 has, in the part where the golf ball 10 impacts, the observation hole 21 whose area S in the surface 20a (the impact surface 20a) facing the launching means is smaller than the contact area B with the impacting golf ball 10. Note that the contact area B with the golf ball 10 in the contact surface 20a is the contact area B with the golf ball 10 including the area S of the observation hole 21 as illustrated in FIG. 2, and is not the contact area excluding the area S of the observation hole 21.

By shooting the image of the contact state with the golf ball 10 through the observation hole 21, the contact phenomenon with the golf ball, which has been hidden and unobservable, can be recognized. The reason that the area S of the observation hole 21 is smaller than the contact area B with the golf ball 10 is as follows. If the area S of the observation hole 21 is increased, the influence of the observation hole 21 on the golf ball 10 increases, causing a change in spin amount or spin direction of the golf ball 10. This hampers accurate reproduction of the contact phenomenon between the golf ball and the golf club.

The area S of the observation hole 21 is preferably 1% to 40% of the contact area B between the impact plate 20 and the golf ball 10, and more preferably 8% to 35% of the contact area B. By limiting the area S of the observation hole 21 to the range from 1% to 40% of the contact area B, the contact state between the impact plate 20 and the golf ball 10 can be sufficiently observed, and also the influence of the observation hole 21 on the golf ball 10 can be reduced to accurately reproduce the contact phenomenon between the golf ball and the golf club. In the case where the area S is less than 1% of the contact area B, the size of the observation hole 21 may be too small to sufficiently observe the contact state. In the case where the area S exceeds 40% of the contact area B, the influence of the observation hole 21 on the golf ball 10 may be excessively large.

In detail, the observation hole 21 more preferably has a horizontal width X of 1 mm to 10 mm, and particularly preferably has a horizontal width X of 1 mm to 5 mm. With this structure, the contact state between the impact plate 20 and the golf ball 10 can be sufficiently observed, and also the influence of the observation hole 21 on the golf ball 10 can be significantly reduced to more accurately reproduce the contact phenomenon between the golf ball and the golf club.

Here, the width X of the observation hole 21 means the width X in parallel with a placement surface (the surface of the ground or a groundwork) on which the impact plate 20 is placed, and the vertical width Y is the width orthogonal to the horizontal width X in the impact surface 20a. In FIG. 2, the front corresponds to the impact surface 20a, and the bottom corresponds to the placement surface. Accordingly, the width in the right-left direction is the horizontal width X, and the width in the up-down direction is the vertical width Y.

The vertical width Y of the observation hole 21 in the up-down direction is not particularly limited, but is preferably not greater than 30 mm and more preferably not greater than 20 mm in order to reduce the influence of the observation hole 21 on the golf ball 10 to a greater extent.

Table 1 shows the results of investigating the influence of the horizontal width X and vertical width Y of the observation hole 21 on the golf ball 10. As compared with the change rate ($\Delta\omega$) of the amount of spin ($\omega$: the number of rotations per minute (rpm)) of the golf ball depending on the coefficient of kinetic friction in the case where the observation hole 21 was not provided, the change rate ($\Delta\omega$) of the amount of spin in the case where the horizontal width X and vertical width Y of the observation hole 21 were changed was investigated. Here, the amount of spin ($\omega_{high\_\mu}$) when the coefficient of kinetic friction ($\mu$) was 0.20 and the amount of spin ($\omega_{low\_\mu}$) when the coefficient of kinetic friction ($\mu$) was 0.15 were measured, and the change rate ($\Delta\omega$) of the amount of spin was calculated according to the following equation:

$$\Delta\omega = (\omega_{low\_\mu}/\omega_{high\_\mu} - 1) \times 100 (\%).$$

TABLE 1

| Horizontal width X (mm) | Vertical width Y (mm) | $\Delta\omega$ (%) |
| --- | --- | --- |
| No observation hole | | 15 |
| 5 | 5 | 15 |
| 5 | 10 | 16 |
| 5 | 15 | 14 |
| 5 | 20 | 12 |
| 5 | 25 | −22 |
| 5 | 30 | 10 |
| 10 | 5 | −21 |
| 10 | 10 | −7 |
| 10 | 15 | 61 |
| 10 | 20 | 38 |
| 10 | 25 | 97 |
| 10 | 30 | 43 |

Table 1 demonstrates that an increase of the horizontal width X of the observation hole 21 influences the golf ball 10 more than an increase of the vertical width Y of the observation hole 21, and so it is important to control the horizontal width X of the observation hole 21. These results can be provided by the fact that the friction force in the vertical direction is a dominant factor relating to the spin of the golf ball, and the vertical area in the impact surface is reduced due to the increase of the horizontal width.

Figure 8A:
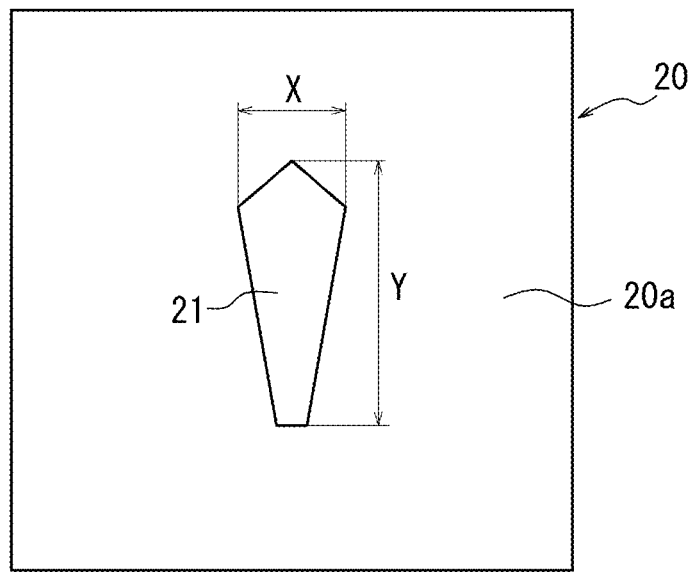
FIGS. 8A and 8B are front views schematically illustrating another embodiment of the impact plate for the golf ball according to the present invention.
Figure 8B:
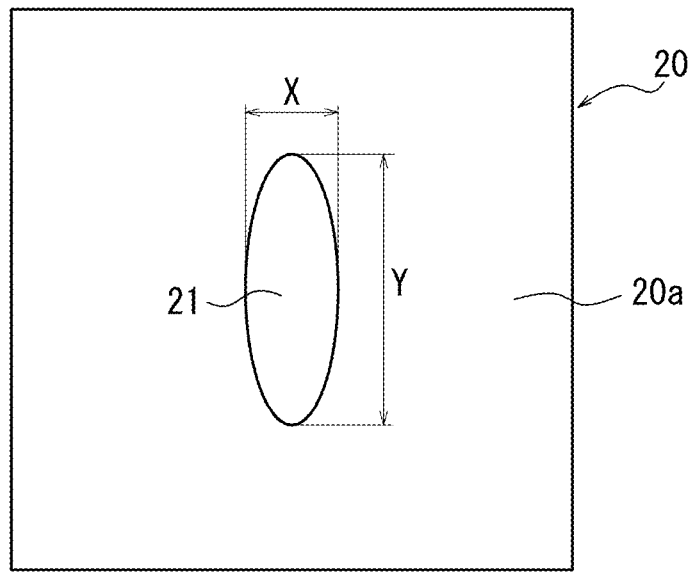

Note that the shape of the observation hole 21 in the impact surface 20a is not limited to a quadrilateral as illustrated in FIG. 2, and may be a polygon (e.g. a pentagon, a hexagon) as illustrated in FIG. 8A or an ellipse as illustrated in FIG. 8B. The horizontal width X of the observation hole 21 in such cases is the maximum width in parallel with a placement surface (the surface of the ground or a groundwork) on which the impact plate 20 is placed, as illustrated in FIG. 8A and FIG. 8B.

Figure 3:
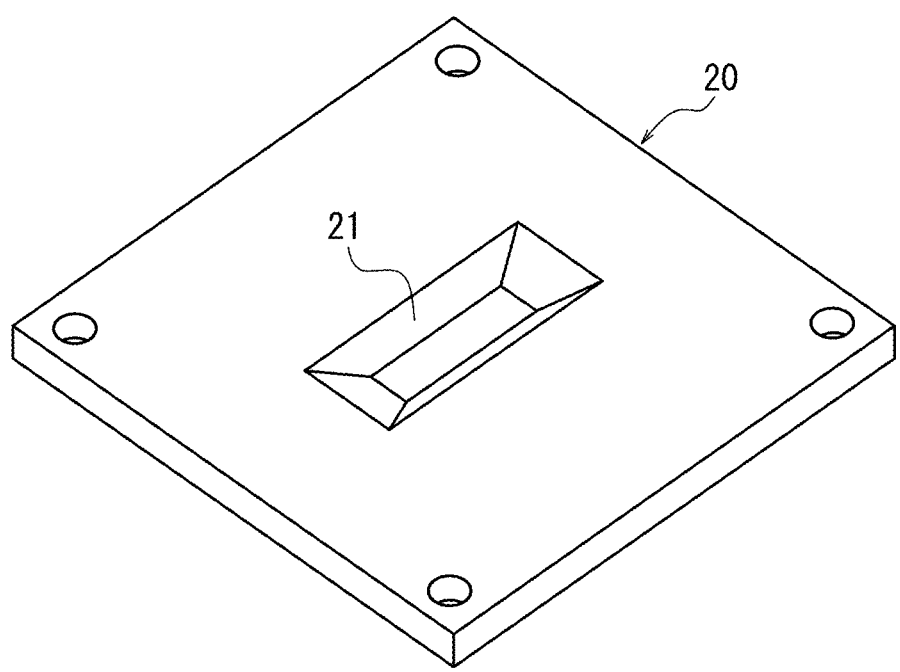
FIG. 3 is a perspective view of the impact plate in the embodiment of the contact state observation apparatus of golf ball according to the present invention.

The observation hole 21 is preferably tapered in the impact plate 20 from the surface facing the imaging means toward the surface (the impact surface 20a) facing the launching means, as illustrated in FIGS. 1 and 3. FIG. 3 illustrates the impact plate 20 as seen from the imaging means side. By tapering the observation hole 21, the area of the observation hole 21 in the surface (the impact surface 20a) facing the launching means, where the golf ball 10 impacts, can be reduced to minimize the influence of the observation hole 21 on the golf ball 10, whereas the area of the observation hole 21 in the surface facing the imaging means can be increased to admit a sufficient amount of light to enable imaging under more favorable conditions.

The tapered shape of the observation hole 21 is not particularly limited as long as the observation hole 21 becomes narrower from the surface facing the imaging means toward the surface (the impact surface 20a) facing the launching means. The observation hole 21 may be tapered so that the cross-sectional area of the observation hole 21 is regularly reduced toward the surface (the impact surface 20a) facing the launching means as illustrated in FIG. 1, or tapered so that the cross-sectional area of the observation hole 21 is irregularly reduced toward the surface (the impact surface 20a) facing the launching means (not illustrated).

The observation hole 21 is preferably filled with a transparent material. This reduces the influence of the observation hole 21 on the golf ball 10 to a greater extent. In the case where the observation hole 21 is not filled with the transparent material, the impacting golf ball 10 may push into the observation hole 21, affecting the amount of spin and the like.

Since the imaging means 30 shoots the image of the contact state of the golf ball through the observation hole 21, the transparent material is used as the filling material so as not to adversely affect the imaging. The transparent material mentioned here need not necessarily be completely colorless and transparent, and may be colored or cloudy to such an extent that allows the imaging means 30 to shoot the image of the contact state of the golf ball 10 through the material.

Examples of the material that has a sufficient strength to withstand the impact of the golf ball 10 and is transparent include acrylic glass, polycarbonate, and ABS.

The material forming the impact plate 20 is not particularly limited, and various materials may be used corresponding to the golf club whose contact state with the golf ball is to be observed. For more accurate reproduction of the contact phenomenon between the golf ball and the golf club, the contact surface 20a of the impact plate 20 with the golf ball 10 is preferably processed corresponding to the intended golf club. The processing mentioned here means to change the properties of the impact surface 20a of the impact plate 20 corresponding to the intended golf club's face, and includes, for example, processing the impact surface 20a to have the same coefficient of friction or grooves as the golf club's face, forming the impact surface 20a with the same material as the golf club's face, and surface roughening treatment by any vertical grooving, horizontal grooving, or sandblasting.

Imaging Means

The contact state observation apparatus of golf ball according to the present invention includes the imaging means 30, provided opposite to the launching means with the impact plate 20 in between, for shooting the image of the contact state between the golf ball 10 and the impact plate 20 at the time of impact of the golf ball 10 through the observation hole 21.

The imaging means 30 is not particularly limited as long as it is capable of short-time imaging at the time of impact of the golf ball 10. For example, a commercially available high-speed camera may be used.

The distance between the observation plate 20 and the imaging means 30 is not particularly limited, and may be changed as appropriate depending on the size of the observation hole 21 and the like. For example, the distance may be in a range from 10 mm to 1000 mm.

Other Features

The contact state observation apparatus of golf ball according to the present invention preferably further includes a two-component force meter (not illustrated) for measuring the force at the time of impact between the impact plate and the golf ball. By measuring the force acting in the normal direction of the surface of the golf ball 10 and in the direction orthogonal to the normal direction in addition to observing the contact state between the golf ball 10 and the impact plate 20, the state of the golf ball 10 at the time of impact can be recognized more accurately. The placement position of the two-component force meter is not particularly limited, and may be, for example, in a support unit of the apparatus.

Figure 4:
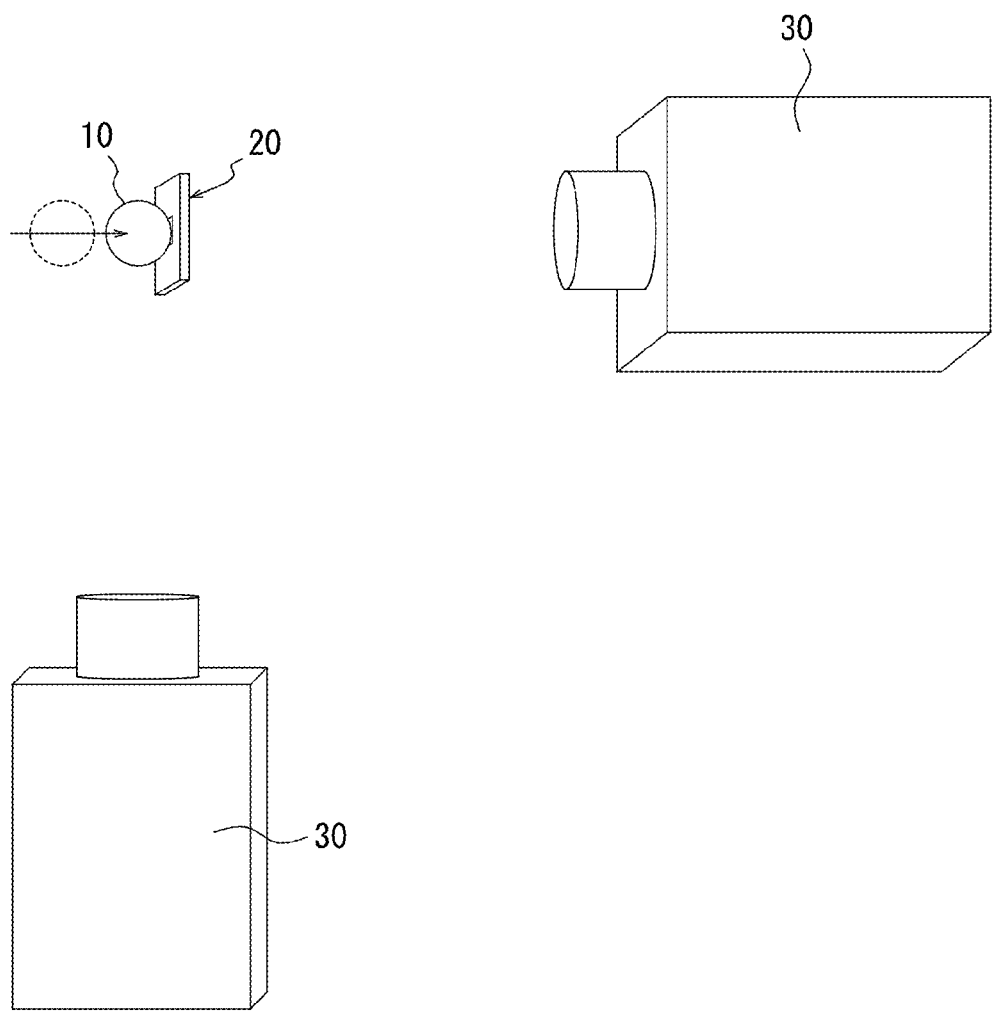
FIG. 4 is a top view schematically illustrating another embodiment of the contact state observation apparatus of golf ball according to the present invention.

The contact state between the golf ball 10 and the impact plate 20 may be observed not only from the front but also from the side, as illustrated in FIGS. 4 and 5.

The placement state of the impact plate 20 is not particularly limited. For example, the impact plate 20 may be placed corresponding to the loft angle and face angle of the face of the intended golf club head, as illustrated in FIGS. 1, 4, and 5.

The golf ball 10 may have a marker to indicate its position. The position of the golf ball before and after impacting with the impact plate 20 can be specified in this way.

(Contact State Observation Method of Golf Ball)

An embodiment of a contact state observation method of golf ball according to the present invention is described next.

As illustrated in FIG. 1, the contact state observation method of golf ball according to the present invention is a method of launching the golf ball 10, causing the launched golf ball 10 to impact the impact plate 20, and observing the contact state of the golf ball 10 with the impact plate 20 at the time of impact, wherein the observation hole 21 whose area is smaller than the contact area with the impacting golf ball 10 is formed in the part of the impact plate 20 where the golf ball 10 impacts, and the contact state of the golf ball 10 is observed through the observation hole 21.

By observing the contact state between the golf ball 10 and the impact plate 20 through the observation hole 21, the contact phenomenon with the golf ball, which has been conventionally hidden and unobservable, can be reliably observed. In addition, by changing the properties of the surface (contact surface) of the impact plate impacting with the golf ball corresponding to the intended golf club as required, the contact state between the actual golf club and golf ball can be reproduced with high accuracy.

Note that the method of launching the golf ball and the method of observing the contact state of the golf ball are not particularly limited, and for example a commercially available golf ball launcher, high-speed camera, etc. may be used. The structure of the impact plate 20 is the same as that described with regard to the contact state observation apparatus of golf ball according to the present invention.

EXAMPLES

The present invention is described in more detail below by way of examples, yet the present invention is not limited to these examples.

As illustrated in FIGS. 4 and 5, the contact state observation apparatus of golf ball that includes: the launching means (not illustrated) for launching the golf ball 10; the impact plate 20 with which the launched golf ball 10 impacts; and the imaging means 30 for shooting the image of the contact state between the golf ball 10 and the impact plate 20 was produced, and the contact state of the golf ball was observed.

As the launching means, a tester (made by Automated Design Corporation in the U.S.) for pneumatically launching balls was used, with the rate of impingement on the impact plate 20 being 43 m/sec.

As the imaging means, a high-speed camera (made by Photron Limited) was used to observe the contact state of the golf ball. Further, the state (initial velocity, spin, hitting angle) of the golf ball 10 before and after the impact with the impact plate 20 was measured using a measuring instrument (SCIENCE EYE FIELD made by Bridgestone Sports Co., Ltd.), and analyzed using a video analyzer (TEMA made by Photron Limited) to track the trajectory of the marker of the golf ball.

As the impact plate 20, a stainless steel plate with a thickness of 10 mm was used, with the observation hole 21 being shaped as a rectangle of 20 mm in vertical width and 5 mm in horizontal width and tapered from the surface facing the imaging means toward the surface facing the launching means. The impact plate 20 was placed in a state of being tilted at 12° with respect to the vertical direction.

Figure 6A:
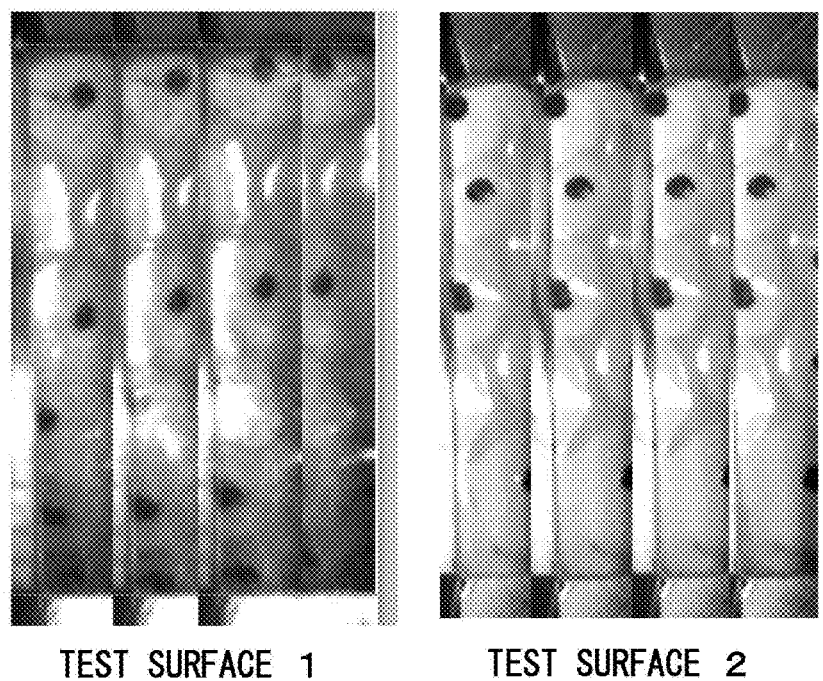
FIG. 6A is a photograph of the contact state between the golf ball and the impact plate taken from the front.
Figure 6B:
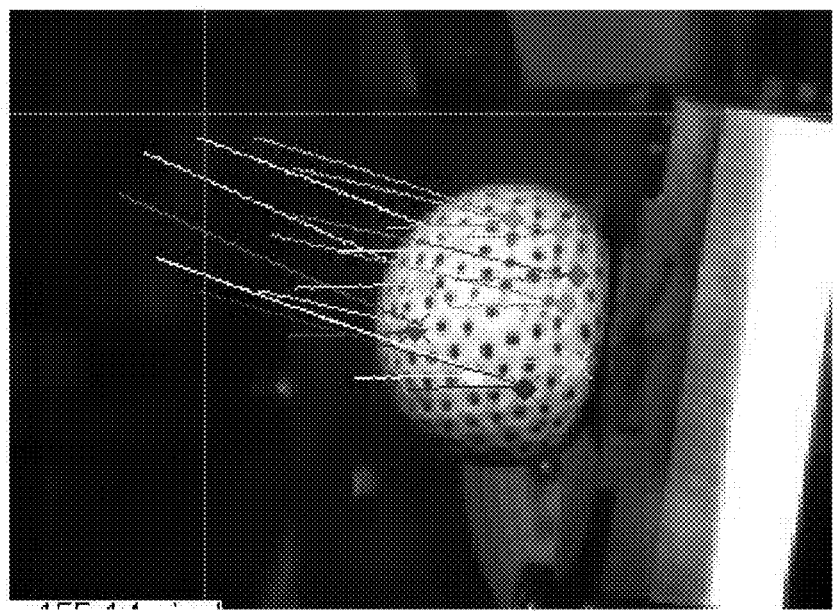
FIG. 6B is a photograph of the contact state between the golf ball and the impact plate taken from the side.

FIG. 6A and FIG. 6B illustrate the observed contact state between the golf ball 10 and the impact plate 20 from the front and from the side, respectively.

Figure 7A:
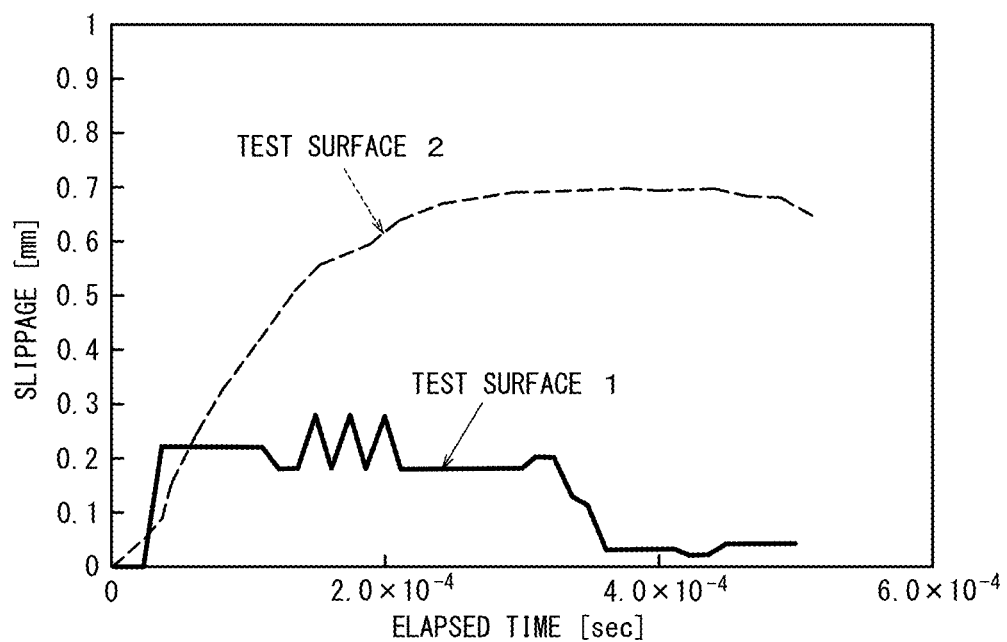
FIG. 7A is a diagram illustrating the temporal changes of the slippage (mm) of the golf ball.
Figure 7B:
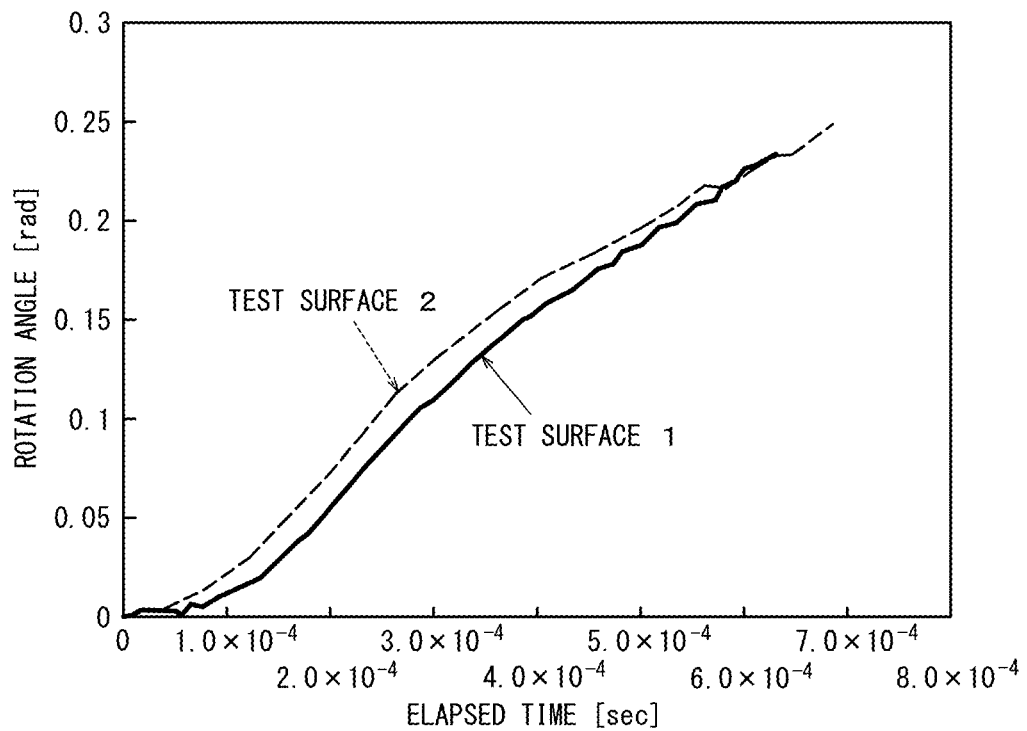
FIG. 7B is a diagram illustrating the temporal changes of the rotation angle (rad) of the golf ball.

Regarding the analyzed behavior of the golf ball, FIG. 7A illustrates the temporal changes of the slippage (mm) of the golf ball, and FIG. 7B illustrates the temporal changes of the rotation angle (rad) of the golf ball. In FIG. 7, a test surface 1 is a surface roughened by sandblasting, and a test surface 2 is a surface coated with a solid lubricant. The temporal changes of the rotation angle of the golf ball cumulatively indicate, for the rotation angle (rad) of the golf ball per unit time, how much the golf ball rotated over time.

The results in FIG. 6A indicate that the contact state on the contact surface between the golf ball 10 and the impact plate 20 was able to be observed. As illustrated in FIG. 6B, the contact state between the golf ball 10 and the impact plate 20 was also able to be observed from the side.

Moreover, as illustrated in FIG. 7A, the golf ball was observed to either stay on the test surface or slip on the test surface depending on the coefficient of friction of the surface (the test surface 1 and the test surface 2). As illustrated in FIG. 7B, this difference in motion affected the spin of the golf ball. The behavior of the golf ball can thus be understood in more detail.

INDUSTRIAL APPLICABILITY

According to the present invention, it is possible to provide a contact state observation apparatus of golf ball and a contact state observation method of golf ball that can observe the contact phenomenon between a golf ball and a golf club which has been conventionally hidden and unobservable.

REFERENCE SIGNS LIST 10 golf ball
20 impact plate
21 observation hole
30 imaging means
S area of observation hole
B contact area between impact plate and golf ball
X horizontal width
Y vertical width

The invention claimed is:

1. A contact state observation apparatus of golf ball comprising:
    launching means for launching a golf ball;
    an impact plate with which the launched golf ball impacts; and
    imaging means, provided ahead of a launching direction of the golf ball and opposite to the launching means across the impact plate, and facing the opposite direction of the launching direction of the golf ball, for shooting an image of a contact state between the golf ball and the impact plate at the time of impact of the golf ball,
    wherein the impact plate has, in a part where the golf ball impacts, an observation hole whose area in a surface facing the launching means is smaller than a contact area with the impacting golf ball, and
    the imaging means shoots the image of the contact state of the golf ball through the observation hole to observe the contact phenomenon of the golf ball.

2. The contact state observation apparatus of golf ball according to claim 1, wherein the area of the observation hole is 1% to 40% of the contact area with the impacting golf ball.

3. The contact state observation apparatus of golf ball according to claim 2, wherein the observation hole has a horizontal width of 1 mm to 10 mm.

4. The contact state observation apparatus of golf ball according to claim 1, wherein the observation hole is tapered in the impact plate from a surface facing the imaging means toward the surface facing the launching means.

5. The contact state observation apparatus of golf ball according to claim 1, wherein the observation hole is filled with a transparent material.

6. The contact state observation apparatus of golf ball according to claim 1, wherein the surface of the impact plate facing the launching means is processed corresponding to a surface shape of a golf club.

7. The contact state observation apparatus of golf ball according to claim 1, further comprising
    a load meter for measuring a force at the time of impact between the impact plate and the golf ball.

* * * * *